(12) United States Patent
Klingelhoefer et al.

(10) Patent No.: US 12,031,107 B2
(45) Date of Patent: Jul. 9, 2024

(54) ENERGY EFFICIENT BIODIESEL PRODUCTION FROM NATURAL OR INDUSTRIAL WASTE OIL

(71) Applicant: BASF SE, Ludwigshafen (DE)

(72) Inventors: Paul Klingelhoefer, Ludwigshafen (DE); Michael Schier, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 17/917,514

(22) PCT Filed: Mar. 30, 2021

(86) PCT No.: PCT/EP2021/058362
§ 371 (c)(1),
(2) Date: Oct. 6, 2022

(87) PCT Pub. No.: WO2021/204610
PCT Pub. Date: Oct. 14, 2021

(65) Prior Publication Data
US 2023/0151299 A1 May 18, 2023

(30) Foreign Application Priority Data
Apr. 7, 2020 (EP) ................................. 20168384

(51) Int. Cl.
*C11C 3/02* (2006.01)
*C10L 1/02* (2006.01)
*C11C 3/10* (2006.01)

(52) U.S. Cl.
CPC ............... *C11C 3/02* (2013.01); *C10L 1/026* (2013.01); *C11C 3/10* (2013.01); *C10L 2200/0476* (2013.01); *C10L 2200/0484* (2013.01)

(58) Field of Classification Search
CPC ......... C07C 67/03; C07C 67/08; C07C 69/52; C10L 1/026; C10L 2200/0476; C10L 2200/0484; C11C 3/003; C11C 3/02; C11C 3/10; Y02E 50/10
See application file for complete search history.

(56) References Cited

U.S. PATENT DOCUMENTS

| 6,822,105 B1 | 11/2004 | Luxem et al. |
| 2004/0209953 A1 | 10/2004 | Wai Lee |
| 2005/0075509 A1 | 4/2005 | Luxem et al. |
| 2016/0230106 A1 | 8/2016 | Ruan et al. |

FOREIGN PATENT DOCUMENTS

| CN | 101880602 A | 11/2010 | |
| CN | 103173293 A | 6/2013 | |
| CN | 104194946 A | 12/2014 | |
| CN | 104450209 A | 3/2015 | |
| EP | 0658183 A1 | 6/1995 | |
| EP | 0658183 B1 | 3/1997 | |
| EP | 1892232 A1 | 2/2008 | |
| FR | 2929621 A1 | 10/2009 | |
| KR | 1020170043906 A | 4/2017 | |
| WO | 9309212 A1 | 5/1993 | |
| WO | 2008007231 A1 | 1/2008 | |
| WO | WO-2008007231 A1 * | 1/2008 | ............. C07C 67/03 |
| WO | 2009068940 A1 | 6/2009 | |
| WO | 2010141917 A2 | 12/2010 | |
| WO | 2011018228 A1 | 2/2011 | |
| WO | 2020074435 A1 | 4/2020 | |

* cited by examiner

Primary Examiner — Ellen M McAvoy
Assistant Examiner — Chantel Graham
(74) Attorney, Agent, or Firm — ArentFox Schiff LLP

(57) ABSTRACT

A method of producing fatty acid alkyl ester from an organic oil source containing at least one free fatty acid, wherein the vegetable and/or animal waste oil has an acid number of at least 30 mg KOH/g and wherein the method comprises the steps of a) reacting the oil source with glycerol at a temperature, which is at least 110° C. and does not exceed 180° C. during the reaction, in the presence of a catalyst comprising at least methane sulfonic acid or the homo anhydride thereof; and b) acidic transesterification at a temperature, which is at least 110° C. and does not exceed 160° C. during the reaction of the reaction product from step a) with an alkanol; and c) isolating the fatty acid alkyl ester from the reaction product of step b).

18 Claims, No Drawings

ENERGY EFFICIENT BIODIESEL PRODUCTION FROM NATURAL OR INDUSTRIAL WASTE OIL

CROSS-REFERENCE TO RELATED APPLICATIONS

This application is a National Stage Entry of PCT/EP2021/058362, filed Mar. 30, 2021, which claims priority to European application No. 20168384.4, filed Apr. 7, 2020, the disclosures of each of which are hereby incorporated by reference in their entirety.

DESCRIPTION

The present invention relates to a method of producing fatty acid alkyl esters from an organic oil source in order to produce biodiesel.

Biodiesel produced from waste oil is getting more and more attractive as there is no food vs. fuel problem and the waste oil has a significantly lower price compared to vegetable oil which is the dominating feedstock for biodiesel.

Whereas there is an established process to produce biodiesel from vegetable oil (disclosed, for example, in EP 0 658 183 A1) there is so far no such established process to produce biodiesel from waste oil as feedstock as the waste oil can differ highly in quality and composition and therefore continuous mode processes, which are known to be energy efficient are not suitable. The processes used today involve energy consuming process steps like glycerolysis at high temperatures of >200° C. or the purification of methanol during the esterification step by distillation. As the main object in using biodiesel besides renewable feedstock is the reduced carbon dioxide emission, process with lower energy demand would bring cost- and environmental benefits.

The present invention relates to an energy efficient method of producing fatty acid alkyl ester from all kind of waste oil containing at least one free fatty acid (FFA), wherein the waste oil has an acid number of at least 30 mgKOH/g and wherein the method comprises step a) of reacting the oil with glycerol at a temperature, which does not exceed 180° C. during the reaction, in the presence of methane sulfonic acid as catalyst; followed by an acidic transesterification of the reaction product from step a) at a temperature of minimum 110° C. with an alkanol; and isolating the fatty acid alkyl ester from the reaction product of step b).

The advantage of reacting FFA containing oil with glycerol is the shift of the equilibrium to the product side as water is removed from the system and no reverse hydrolysis reaction happens as is the case when using methanol where there will be an equilibrium due to water formation in the esterification step which by current technology is removed by distilling it together with the methanol. By an acidic transesterification step at similar temperature as in the esterification step energy loss by cooling and pH changing as would be the case by using standard alkaline transesterification as e.g. disclosed in EP 0 658 183 A1 is avoided.

WO 2011/018228 A1 describes an acidic transesterification under pressure with methanol or ethanol in the manufacture of biodiesel wherein methane sulfonic acid is used as a catalyst. However, the described process needs a low free fatty acid feed, preferred is vegetable oil.

EP 1 892 232 A1 describes the production of esters of fatty acids and lower alcohols. However, temperatures of 200° C. to 280° C. are used and transesterification is done using an alkaline catalyst. However, the high temperature is cost- and energy intensive and causes side products.

FR 2 929 621 A1 describes the usage of methane sulfonic acid to esterify fatty acids and glycerol is mentioned as an alcohol for the esterification. However, temperature for esterification is at temperatures of 45° C. to 70° C. Biodiesel can be produced by further transesterification.

WO 2008/007231 A1 and WO 2009/068940 A1 describe an esterification process of fatty acid substances with glycerol in the presence of various catalysts and a reaction end temperature of about 230° C. However, the high temperature is cost- and energy intensive and causes side products.

US 2004/0209953 A1 describes different glyceride compositions and the making thereof.

KR 10-2017-0043906 A describes a method for converting High Acid Value Fatty Acid to Bio Fuel Oil or Biodiesel, wherein a fatty acid is converted into a fat oil by adding glycerol in the presence of sulfuric acid or methane sulfonic acid at 200-250° C.

US 2016/0230106 A1 describes the acidification of waste oil compositions by acid washing to produce a composition comprising free fatty acids derived from the waste oil composition and converting the same into glycerides followed by transesterification to yield a biodiesel composition. However, a catalyst free reaction results in uncomplete reaction or harsh reaction conditions which causes side product formation. US 2005/075509 A1 also describes a process starting with the reaction of glycerides and free fatty acids with glycerol without catalyst and subsequent transesterification.

U.S. Pat. No. 6,822,105 B1 describes a process starting with the reaction of glycerides and free fatty acids with glycerol in the presence of a catalyst selected from organotin compounds, organo titanium compounds, alkali acetates, earth alkali acetates, lewis acids, alkali carbonates, earth alkali carbonates, and combinations thereof and subsequent transesterification. However, the mentioned metal containing catalysts are expensive and result in additional process steps to remove undesired metal salts.

CN 104450209 A describes a method for reducing the acid value of crude rice bran oil through solid super acid catalysis. The method comprises the following steps: adding glycerol and a solid super acid catalyst into crude rice bran oil with a high acid value, heating, stirring, vacuuming to remove water generated from reaction, after the reaction is completed, filtering and recycling the catalyst, thereby obtaining rice bran oil with a low acid value. However, the use of solid super acid catalysts is expensive.

CN 101880602 A describes the esterification of high acid value oil using high acid value oil as raw material, adding a solid catalyst, adding crude glycerol to the high acid value oil by a dropping method and refluxing the esterification reaction under vacuum condition. However, the use of solid catalysts results in more complicated reaction equipment due to the heterogeneous phase system.

WO 2010/141917 A2 describes the producing of biodiesel oil starting from a raw material comprising a fatty acid and oil, which is contacted with glycerol and a Lewis acid catalyst in form of TBT (tributyltin) at temperatures between 150 and 200° C. However, such catalysts are expensive.

CN 103173293 A relates to a method for preparing biodiesel by utilizing high-acid value oil. The method comprises the steps of esterifying the raw materials of the high-acid value oil, enabling glycerol and the raw materials of the high-acid value oil to esterify with each other under the catalyzing action of an ionic liquid, and thus obtaining a mixture of a low-acid value esterification product-monoglyceride, diglyceride or triglyceride. Also, CN 104194946 A describes the use of an ionic liquid catalyst. However, the handling of ionic liquids results in high demand regarding the reaction equipment.

International patent application PCT/EP2019/077064 describes the reaction of methane-sulfonic acid with an oil source and glycerol followed by a transesterification step in a preferred alkaline medium.

However, there is a need for even more energy efficient processes that combine the steps of glycerol esterification and transesterification.

Thus, it is an object of the present invention to provide an energy efficient process for biodiesel production from waste oil which avoids or reduce the disadvantageous drawbacks caused by related art processes.

This object is achieved by method of producing fatty acid alkyl ester from an organic oil source containing at least one free fatty acid, wherein the vegetable and/or animal waste oil has an acid number of at least 30 mg KOH/g and wherein the method comprises the steps of a) reacting the oil source with glycerol at a temperature, which is at least 110° C. and does not exceed 180° C. during the reaction, in the presence of a catalyst comprising at least methane sulfonic acid or the homo anhydride thereof, preferably methane-sulfonic acid; and b) acidic transesterification at a temperature, which is at least 110° C. and does not exceed 160° C. during the reaction of the reaction product from step a) with an alkanol; and c) isolating the fatty acid alkyl ester from the reaction product of step b).

Step a) can be preceded by a filtration step in order to remove solid parts from the oil source. Also, a degumming step can be preceded.

Preferably, step a) is carried under reduced pressure.

Preferably, step b) is carried out under pressure. Suitable pressure is from 1.1 bar to 10 bar, preferably, from 1.5 bar to 7.5 bar, preferably from 2 bar to 5 bar, more preferably from 2.5 bar to 4 bar, more preferably from 2.5 bar to 3.5 bar, especially at 3 bar.

Preferably after step b) and before step c) a step b') of removing at least partly the alkanol by using the reaction temperature, especially by lowering the pressure, preferably to atmospheric pressure, is introduced.

Preferably, the alkanol at least partly removed can be recycled by feeding to step b) of the process of the invention.

To improve on the kinetics of step a) and/or step b) the esterification and transesterification can be done as an emulsion e.g. by made ultrasonic cavitation. Step a) and b) can be done in the same reactor at similar temperatures, i.e. in the same temperature range, especially from 110° C. to 160° C., preferably 120° C. to 160° C. Preferably, the difference of the temperature in step a) and step b) differs in at most 40° C., more preferably at most 20° C. and the temperature in step a) is higher than the temperature in step b).

Step c) can include a phase separation that can be preceded by a neutralization step. Accordingly, it is preferred that in step c) the isolation includes a neutralization step.

Useful for neutralization are alkali metal or alkaline earth metal compounds in the form of the oxides, hydroxides, hydrides, carbonates, acetates or alkoxides of the alkanol, preferably sodium hydroxide, potassium hydroxide, or sodium and potassium alkoxides of the short-chain monohydric alcohols having 1 to 5 carbon atoms. The alkaline earth metal compounds are preferably sodium or potassium.

It was surprisingly found that the use of methane sulfonic acid has significant advantages compared to sulfuric acid as there is no insoluble resin formation in the esterification step and less sulfur in the biodiesel from step c).

Methane sulfonic acid as catalyst is advantageous compared to sulfuric acid as common acidic catalyst since no or decreased tendency of decomposition of glycerol or the glycerol esters can be observed due to oxidation, water elimination, addition to any double bond and sulfatation.

The process can be carried out throughout a broad range of oil qualities and different organic oil sources having a content of free fatty acid of at least 15% by weight, which relates to an acid number of about 30 mg KOH/g oil source. After the transesterification step a phase separation step can be carried out with or without removing the alkanol partly or fully.

The starting material in the process of producing fatty acid alkyl esters (FAAE's) is an organic oil source.

Organic oil is produced in contrast to mineral oil by plants, animals and other organisms through natural metabolic processes and is glyceride based. The term "organic oil source" is to be understood to include organic oil, like vegetable oil and animal oil, especially vegetable oil, but also any other mixture, by-product or fraction of organic oil that contains at least one FFA and is suitable to produce biodiesel according to the method of producing FAAE according to the present invention. The term "organic oil source" also includes fats, which are solid at room temperature, but liquid at the reaction temperature in step a) of the method of producing FAAE according to the present invention.

Organic oil sources typically contain different types of free fatty acids in different amounts as well as fatty acid bound as tri-, di- and monoglycerides. Only very low amounts—if any—of other organic acids can be included so that in industry the acid number measurement is used to quantify the amount of all free fatty acids contained in the organic oil source. Measurement can be carried out in analogy of the standard method DIN EN 14104 (2003-10).

The method of the present invention is suitable for organic oil sources with an acid number of at least 30 mg KOH/g oil source. Preferably, the oil source has an acid number of at least 40 mg KOH/g oil source, more preferably at least 60 mg KOH/g oil source, even more preferably at least 80 mg KOH/g oil source, even more preferably at least 100 mg KOH/g oil source, even more preferably at least 120 mg KOH/g oil source, even more preferably at least 140 mg KOH/g oil source, even more preferably at least 150 mg KOH/g oil source.

Organic oil sources include vegetable and animal oils and fats. Vegetable oils are generally obtained by extraction from seeds, by means of solvent or pressure, while animal fats are obtained by hot extraction in autoclaves or by means of solvent. Normally these fatty substances contain free fatty acids, sterols, phospholipids, water, odorous substances and other impurities. Refining of the fatty substances involves complete removal of nearly all the impurities including the free fatty acids so that they can be used in the production of biodiesel, in food and in industry in general.

Refined vegetable and animal oils and fats typically show very low FFA content. However during use of these refined oils and fats the FFA content can increase.

Used oils typically show high amounts of free fatty acid and thus also have high acid numbers. Thus, in a preferred embodiment of the present invention the organic oil source is from used vegetable and/or animal oil and/or fat, like used cooking oil. Used oil is also called waste oil, so that waste oil, especially waste vegetable oil, is preferred.

Other organic oil sources include by-products of the chemical and physical refining of vegetable and/or animal oil and/or fat, by-products of the refining of glycerine from biodiesel, fatty acids from distillation and non-distillation, hydrolytically cleaved fatty substances, trap grease and distilled and non-distilled fatty acids resulting from the cleaving of soaps.

Also mixtures of the above organic oil sources are encompassed.

Preferably, the organic oil source is from used vegetable oil or by-products of the chemical and physical refining of vegetable oil. The vegetable oil is preferably an oil or oil mixture selected from the group of oils consisting of coconut oil, corn oil, cottonseed oil, olive oil, palm oil, peanut oil, rapeseed oil, safflower oil, sesame oil, soybean oil and sunflower oil, preferably the vegetable oil comprises rapeseed oil, even more preferably the vegetable oil is palm oil.

More preferably, the organic oil source is palm fatty acid distillate (PFAD) or palm sludge oil (PSO). PAFD is a lower-value by-product generated during the refining of palm oil in the fatty acid stripping and deodorization stages. PFAD is generally sold as a source of industrial fatty acids for non-food applications.

Even more preferably, the organic oil source is palm sludge oil (PSO). It is an un-distilled residue of palm oil production with inferior quality compared to PFAD.

The organic oil source may be purified before used in step a) of the method for producing FAAE. An optional purification step is the removal of metal ions, e.g. be using complexation agents (chelate formation). Also washing steps may be used before step a). Suitable washing steps include water and acidic washing. This may be used to remove inorganic acids or the like.

Preferably, the at least one free fatty acid is a fatty acid or a mixture of fatty acids selected from the group of fatty acids consisting of caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linolelaidic acid, alpha-linoleic acid, arachidonic acid, eicosapentaenoic acid, erucic acid and docosahexaenoic acid, preferably the at least one free fatty acid comprises or consists of oleic oil and/or palmitic oil. Accordingly, the term "at least one fatty acid" is to be understood in that the at least one fatty acid is specific fatty acid or a mixture of two, three or more fatty acids (mixture of fatty acids).

These fatty acids are converted into alkyl esters to yield FAAE's as biodiesel. However, the most preferred alkyl ester is the methyl ester so that fatty acid methyl esters (FAME's) are preferred. Preferably, the biodiesel obtained by the method of producing FAME according to the present invention fulfills the requirements of DIN EN 14214 (2014-06).

The free fatty acids are converted into alkyl esters to yield FAAE's as biodiesel. However, the most preferred alkyl ester is the methyl ester so that fatty acid methyl esters (FAME's) are preferred.

Preferably, the reaction time in step a) can be reduced by making an emulsion so that the reaction surface of the two-phase system is greatly enhanced.

Since in step a) also water is a reaction product suitable measures should be taken to reduce the water formed by the reaction. Preferably, the reaction in step a) is carried out under reduced pressure (relative to atmospheric pressure).

More preferably, the pressure is below 1000 hPa, more preferably 900 hPa or lower, even more preferably 800 hPa or lower, even more preferably, 700 hPa or lower, even more preferably, 600 hPa or lower, even more preferably 500 hPa or lower, even more preferably 400 hPa or lower, even more preferably 300 hPa or lower, even more preferably 200 hPa or lower, even more preferably 100 hPa or lower.

Preferably, during the reaction in step a) the temperature does not exceed 170° C., more preferably does not exceed 160° C., even more preferably the temperature does not exceed 150° C. Preferably, in step a) the temperature is at least 110° C., more preferably at least 120° C., even more preferably at least 130° C. Accordingly preferred temperature ranges are from 110° C. to 180° C., more preferably the temperature is from 110° C. to 170° C., even more preferably from 120° C. to 160° C. and even more preferably from 130° C. to 150° C. A preferred temperature is 140° C.

Preferably, during the reaction in step b) the temperature does not exceed 160° C., more preferably does not exceed 150° C., even more preferably the temperature does not exceed 140° C. Preferably, in step b) the temperature is at least 110° C., more preferably at least 120° C.

Preferably, in step a) the initial molar ratio of glycerol to free fatty acid calculated on the basis of the acid number of the oil is from 1:2 to 1.2:1, more preferably from 1:2 to 1:1, even more preferably from 3:5 to 9:10, even more preferably from 2:3 to 9:10.

Preferably, in step a), step b) or step a) and step b) the amount of methane sulfonic acid or anhydride thereof is from 0.5 to 1.5 weight-%, even more preferably from 0.75 to 1.25 weight-% based on the total amount of the oil source.

In step b) a transesterification is carried out with an alkanol, preferably methanol to yield FAME. As the acid catalyst is already present no further catalyst addition is needed.

Excess of methanol can be separated and recycled for step b) of the method of producing FAAE according to the present invention.

In step c) the reaction product (biodiesel) is isolated. Any known isolation method can be used. Preferably, in step c) the isolation includes a distillation step, preferably under reduced pressure. This distillation is useful to convert crude biodiesel into biodiesel of higher purity. Before distillation phase separation may be used to recover glycerol, which in tur may be further purified, e.g. also by distillation.

In preferred embodiment between step a) and step b) no phase separation is carried out. It is also preferred when step a) and step b) are carried out in the same reactor vessel.

EXAMPLES

Analytical Details:

Waste Oil Characterization:

Appearance: black liquor containing dark brown sludge sediment

Viscosity (Brookfield, rt): 36.8 mPa*s (60 rpm/Spindel1/23°

Iodine number: 101.8 gI$_2$/100 g

Acid number: 140 mgKOH/g a)

1. Step: Filtration

Waste oil was filtered two times at rt via paper filter (1.6-2 µm). Residue: appr. <1 wt %

Water content after filtration: 0.5%

2. Step:

Acidic Degumming and Esterification 500 g filtered waste oil, 5 g water, 105 g Glycerol and 4 g Lutropur MSA (methane sulfonic acid, 70% active content) were mixed in a reaction vessel and heated up to 140° C. under vacuum which was kept constant at 10 kPa. Reaction time was 4 h.

Analytical Result:

TABLE 1

Time dependency of Acid number in mgKOH/g
The esterification of free fatty acid with glycerol was controlled by taking out samples (approx. 4 g). The sample is washed with ca. 4 g glycerol to eliminate MSA from the mixture. Glycerol and oil phase are separated. From the oil phase the acid number is measured according to DIN EN 14104.

| | 0 h | 0.5 h | 1.0 h | 2.0 h | 3.0 h | 4.0 h |
|---|---|---|---|---|---|---|
| Example 1 | 102 | 41 | 20 | 17 | 15 | 14 |

After reaction 552 g reaction product was obtained from step 2 and 28 g distillate (mainly water).

Process a) was done two times to get enough raw material for b).

b)

3. Step:

Acidic Transesterification 745 g reaction product from a) and 223 g methanol (30 wt % related to oil) was filled in a pressure reactor and heated up to 120° C. and stirred. Reaction pressure was 3*10$^5$ Pa. Reaction time was 3 h. After 3 h reactor was cooled down.

Analytical Results:

806 g reaction product was obtained (missing product weight is due to control of acid number during the reaction—4 times)

Acid number (determined as described in Tab. 1) after 3 h was 10 mgKOH/g.

c)

4. Step

Product resulting from b) was shift to a distillation column and heated to 130° C. under stirring at atmospheric pressure.

23 g methanol was distilled.

5. Step 772 g reaction product was neutralized with 6.9 g NaOH (40% concentration) and phase separated in a separating funnel which is difficult as there is no visual difference in the phase (all black). Separation finish was judged by change of viscosity.

Analytical Results:

Lower phase (glycerol/MSA phase and residual methanol from step 2) was 144 g.

Upper phase (fatty acid methyl ester) from step 2) was 623 g.

6. Step

Fatty acid methyl ester phase was centrifuged but only little residue was observed.

7. Step

Purification of the fatty acid methyl ester after centrifuge is done by distillation at approx.

3 hPa and temperature of approx. 210° C.

Sulfur content of fatty acid methyl ester from step 7:

Distilled fatty acid methyl esters (biodiesel): <10 ppm sulfur.

The invention claimed is:

1. A method of producing fatty acid alkyl ester from an organic oil source comprising at least one free fatty acid, wherein the organic oil source has an acid number of at least 30 mg KOH/g and wherein the method comprises the steps of
    a) reacting the oil source with glycerol at a temperature, which is at least 110° C. and does not exceed 180° C. during the reaction, in the presence of a catalyst comprising at least methane sulfonic acid or the homo anhydride thereof;
    b) acidic transesterification at a temperature, which is at least 110° C. and does not exceed 160° C. during the reaction of the reaction product from step a) with an alkanol; and
    c) isolating the fatty acid alkyl ester from the reaction product of step b).

2. The method of claim 1, wherein the fatty acid alkyl ester is fatty acid methyl ester.

3. The method of claim 1, wherein the organic oil source is from used vegetable and/or animal oil and/or fat, by-products of the chemical and physical refining of vegetable and/or animal oil and/or fat, by-products of the refining of glycerol from biodiesel, fatty acids from distillation and non-distillation, trap grease, hydrolytically cleaved fatty substances distilled and non-distilled fatty acids resulting from the cleaving of soap or mixtures thereof.

4. The method of claim 1, wherein the organic oil source has an acid number of at least 40 mg KOH/g oil source.

5. The method of claim 1, wherein in step a) the temperature does not exceed 170° C.

6. The method of claim 1, wherein in step a) the temperature is at least 120° C.

7. The method of claim 1, wherein in step b) the temperature does not exceed 160° C.

8. The method of claim 1, wherein in step b) the temperature is at least 115° C.

9. The method of claim 1, wherein in step a) the initial molar ratio of glycerol to free fatty acid calculated on the basis of the acid number of the oil is from 1:2 to 1.2:1.

10. The method of claim 1, wherein in step a), step b) or step a) and b) the amount of the methane sulfonic acid or anhydride thereof is from 0.5 to 1.5 weight-% based on the total amount of the oil source.

11. The method of claim 1, wherein in step c) the isolation comprises a neutralization step.

12. The method of claim 1, wherein in step c) the isolation comprises a distillation step.

13. The method of claim 12, wherein the distillation in step c) is carried out under reduced pressure.

14. The method of claim 1, wherein between step a) and step b) no phase separation is carried out.

15. The method of claim 1, wherein step a) and step b) are carried out in the same reactor vessel.

16. The method of claim 1, wherein after step b) and before step c) a step b') of removing at least partly the alkanol by using the reaction temperature is introduced.

17. The method of claim 16, wherein step b') comprises lowering pressure of the reaction.

18. The method of claim 16, wherein step b') comprises lowering atmospheric pressure of the reaction.

* * * * *